(12) United States Patent
Alhuwaishel (10) Patent No.: US 8,669,863 B2
(45) Date of Patent: Mar. 11, 2014

(54) MEDICAL INFORMATION BAND (76) Inventor: Fahad M. F. S. Alhuwaishel, Hadiya (KW)

( * ) Notice: Subject to any disclaimer, the term of this patent is extended or adjusted under 35 U.S.C. 154(b) by 158 days.

(21) Appl. No.: 13/460,615

(22) Filed: Apr. 30, 2012

(65) Prior Publication Data

US 2013/0169431 A1 Jul. 4, 2013

Related U.S. Application Data (60) Provisional application No. 61/582,802, filed on Jan. 3, 2012.

(51) Int. Cl.
*G08B 1/08* (2006.01)
(52) U.S. Cl.
USPC ............ 340/539.11; 340/539.12; 340/539.22; 345/1.1; 368/227; 600/300; 600/301; 705/3
(58) Field of Classification Search
USPC .......... 340/539.12, 539.22; 345/1.1; 368/227; 600/300, 301; 705/3
See application file for complete search history.

(56) References Cited

U.S. PATENT DOCUMENTS

| | | | |
|---|---|---|---|
| 4,312,296 A | 1/1982 | Stelleman et al. | |
| 4,744,331 A | 5/1988 | Whiffin | |
| 5,012,229 A * | 4/1991 | Lennon et al. | 345/1.1 |
| 8,401,873 B2 * | 3/2013 | Brown et al. | 705/3 |
| 2008/0000429 A1 | 1/2008 | Page | |
| 2008/0001735 A1 * | 1/2008 | Tran | 340/539.22 |
| 2008/0062821 A1 * | 3/2008 | Yan | 368/227 |
| 2009/0318779 A1 * | 12/2009 | Tran | 600/301 |
| 2009/0322513 A1 * | 12/2009 | Hwang et al. | 340/539.12 |
| 2011/0093296 A1 * | 4/2011 | Klink | 705/3 |
| 2011/0152632 A1 * | 6/2011 | Le Neel et al. | 600/300 |
| 2011/0315085 A1 | 12/2011 | Lindgren | |
| 2012/0006277 A1 | 1/2012 | Troy et al. | |
| 2012/0191476 A1 * | 7/2012 | Reid et al. | 705/3 |

* cited by examiner

*Primary Examiner* — Daniel Wu
*Assistant Examiner* — Israel Daramola
(74) *Attorney, Agent, or Firm* — Richard C. Litman (57) ABSTRACT

The medical information band is an electronic control unit removably attached to a band that may be worn by a user or attached to a medication bottle. The electronic control unit displays all the information of drugs that the user takes, and provides an electronic alert to remind the user when to take the medication, or when the medication has reached its expiration date. The electronic control unit includes a temperature sensor, and alerts the user when the medication must be moved to a different location with a more appropriate storage temperature. Moreover, the electronic control unit may also display the personal information and the health status of the user.

17 Claims, 10 Drawing Sheets

| File |
|---|
| Exp Date: Saturday, October 22, 2011 ∨ Days Remaining: 3 |
| Courses: 3 <> |
| Personal Information: |
| Health Status |
| Uploading Process: |

Upload

*Fig. 4*

File

Exp Date: Saturday , October 22, 2011    [v] Days Remaining: 3

Courses: [3] [<>]

Personal Information: Name: Fahad  Age: 24  Blood type: O+

Health Status

Uploading Process:

Upload

| File | |
|---|---|
| Exp Date: | Saturday , October 22, 2011 ◁▷ Days Remaining: 3 |
| Courses: | 3 |
| Personal Information: | Name: Fahad  Age: 24  Blood type: O+ |
| Health Status | Permanent Diseases: Diabetic  Disease History: had a heart attack twice |
| Uploading Process: | |

Upload

MEDICAL INFORMATION BAND

CROSS-REFERENCE TO RELATED APPLICATION

This application claims the benefit of U.S. Provisional Patent Application Ser. No. 61/582,802, filed Jan. 3, 2012.

BACKGROUND OF THE INVENTION

1. Field of the Invention

The present invention relates to apparatus for prompting patients to take medication at prescribed times, and more particularly to medical information band that provides an electronic medical and prescription information storage band automatically programmable by the user or a health care professional.

2. Description of the Related Art

Personal medical information devices of a variety of designs and configurations have failed to provide convenient functionality for users of such devices. More specifically, such previous devices have not addressed the unfulfilled need to display a variety of wearer body parameters, not just temperature only. Moreover, a variety of casings that could not only be worn by the user, but could also be attached to the drugs, would also be desirable. Additionally, calendars and alerts would be desirable.

Thus, an electronic medical and prescription information storage band solving the aforementioned problems is desired.

SUMMARY OF THE INVENTION

The medical information band is an electronic medical and prescription information storage band having an electronic circuit added to a band in order to make it a medical band. The band displays all the information of the drugs the users take. Moreover, the band also displays the personal information and the health status of the user.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
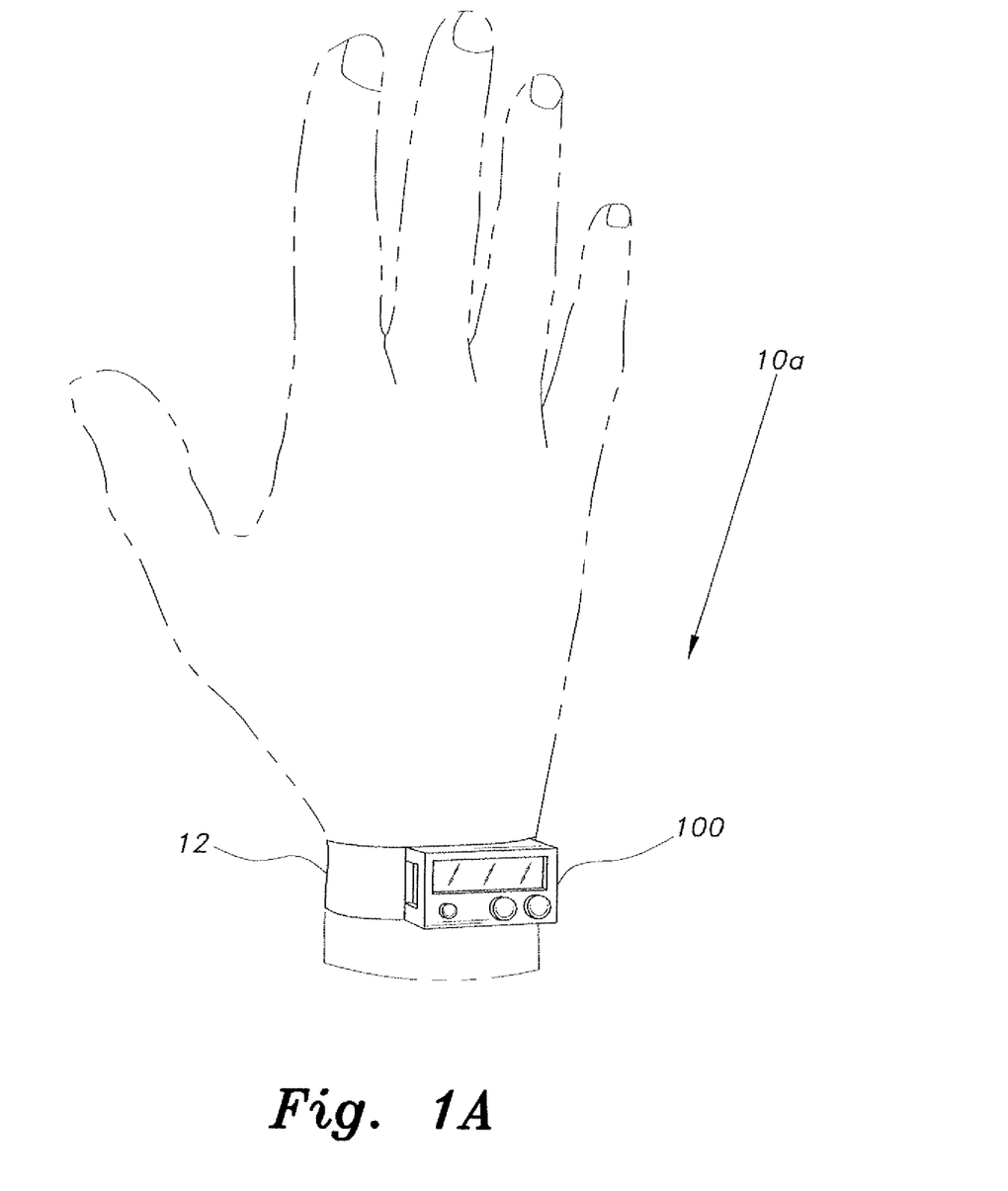
FIG. 1A is an environmental perspective view of a medical information band according to the present invention, shown disposed on a wearer.
Figure 1B:
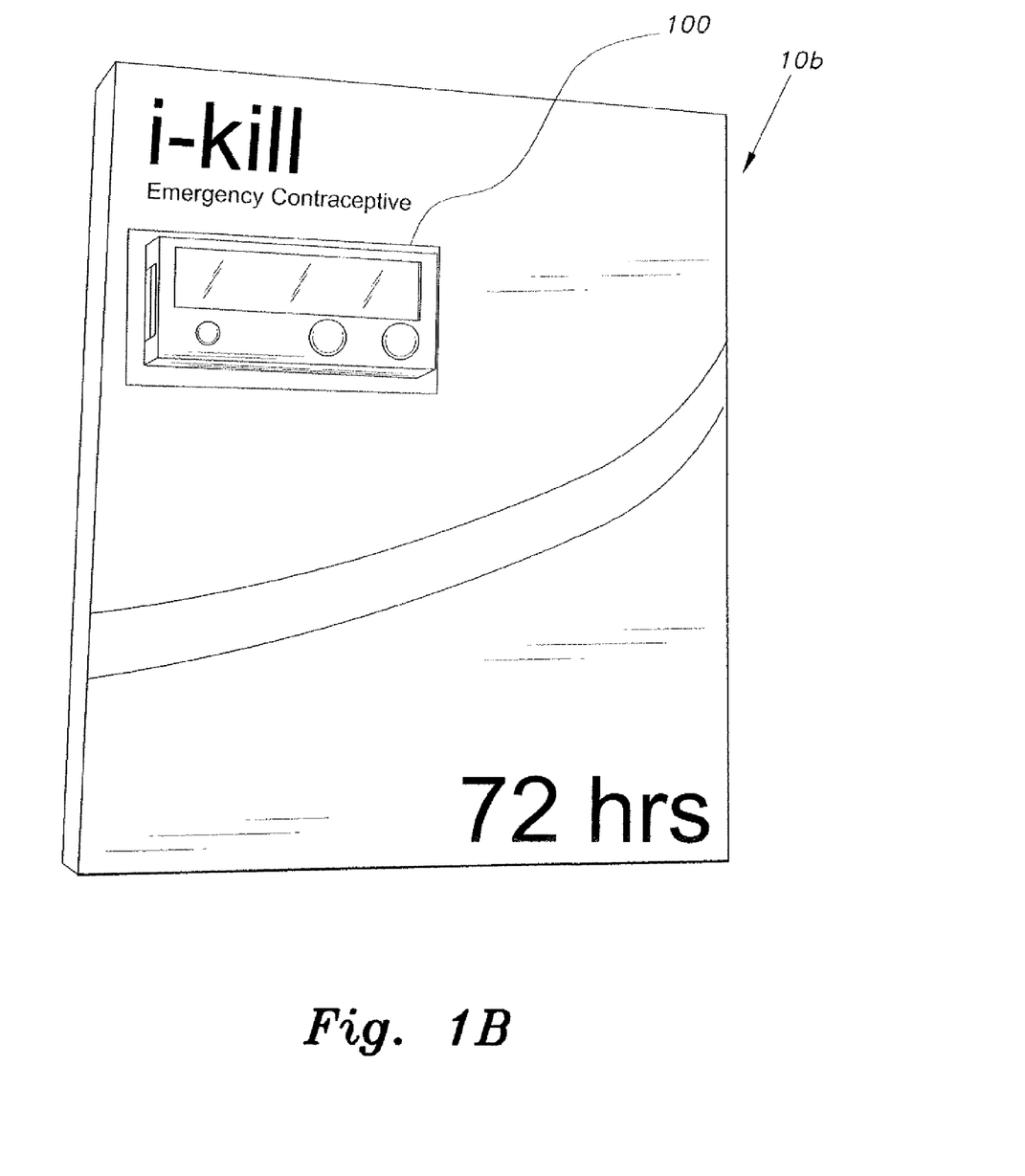
FIG. 1B is an environmental perspective view of the electronic control unit of the medical information band of FIG. 1, shown removed from the band and attached to a pill box.
Figure 1C:
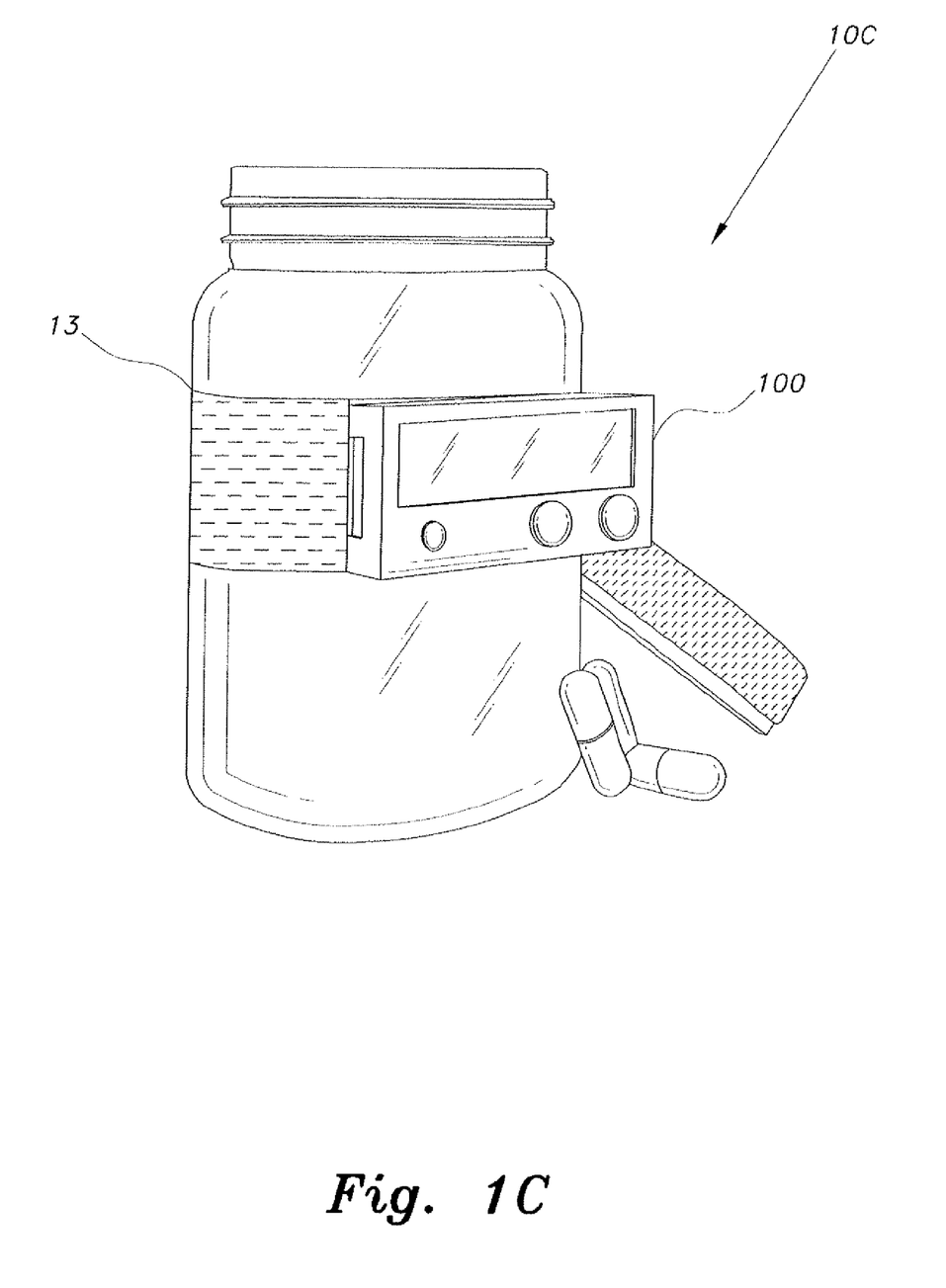
FIG. 1C is an environmental perspective view of a medical information band according to the present invention, shown disposed on a pill bottle.

The electronic medical and prescription information storage band 10a includes an electronic control unit 100 added to a band 12 to make a medical information band, as shown in FIG. 1A. As shown in FIG. 1B, in an alternative configuration 10b, the electronic control unit 100 can be removed from the band 12 and placed on a pharmaceutical package via, e.g., adhesive means. As shown in FIG. 1C, in another configuration 10c, the electronic control unit 100 may be attached to a pill bottle with a modified elastic band 13 adapted for fitting pill bottles.

Figure 1D:
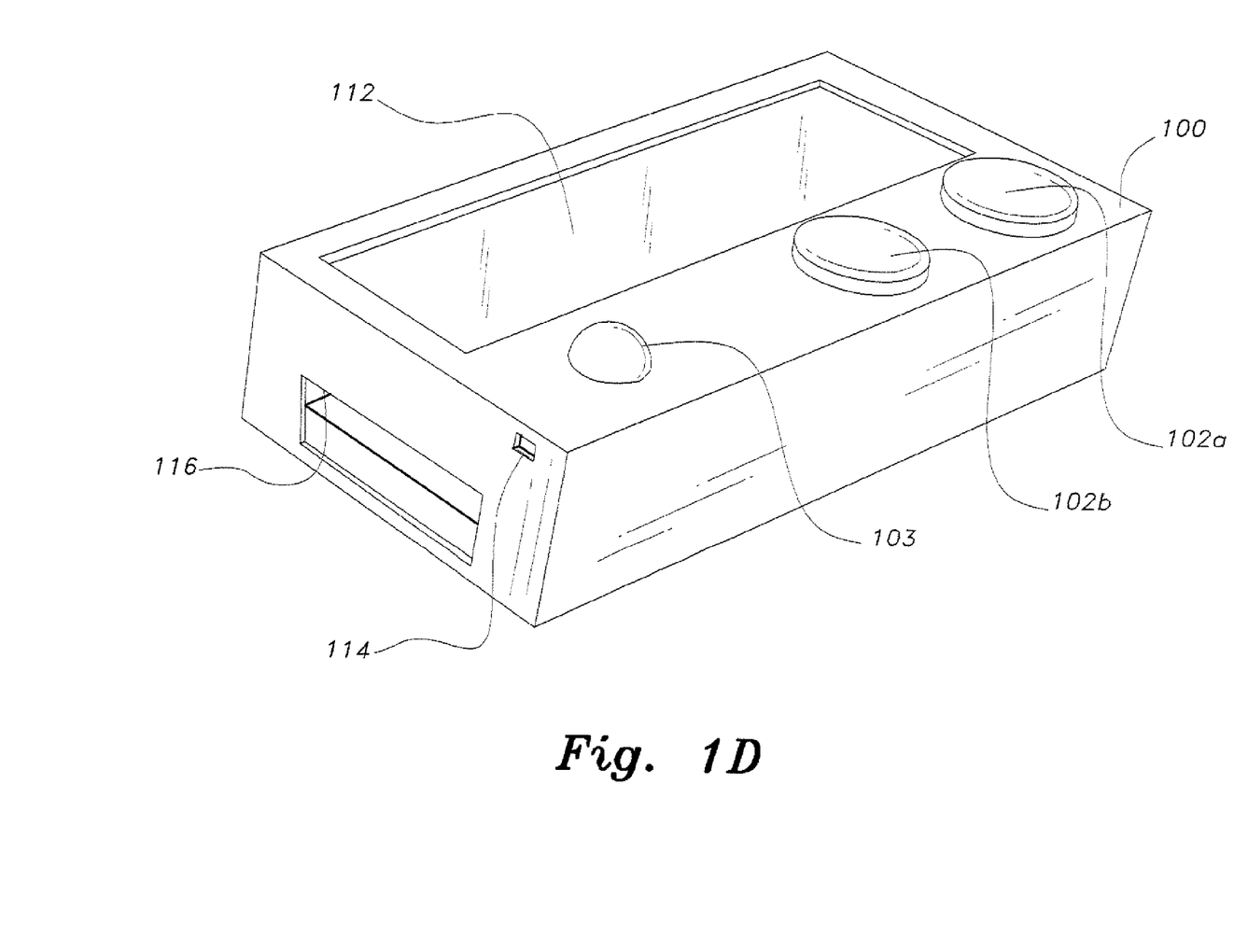
FIG. 1D is a perspective view of the electronic control unit of a medical information band according to the present invention.

FIG. 1D most clearly shows the housing of the electronic control unit 100 having push buttons 102a and 182b, generally functioning as menu or value increment and decrement buttons, respectively. The substantially rectangular shaped housing has a mini LCD display 112 or OLED on its top face. LED lights 103 are also disposed on the top face of the housing. A side of the substantially rectangular housing of the electronic control unit 100 may also have an In-Circuit Serial Programming (ICSP) or Universal Serial Bus (USB) port 114, or RFID for wireless connection (without the need of a rectangular port in this case), for programming the internal electronic circuit. A rectangular cavity 116 extending end-to-end through the electronic control unit 100 is provided for a variety of band fasteners to allow a user to wear the device on a user's limbs, e.g., an arm or wrist.

Figure 1E:
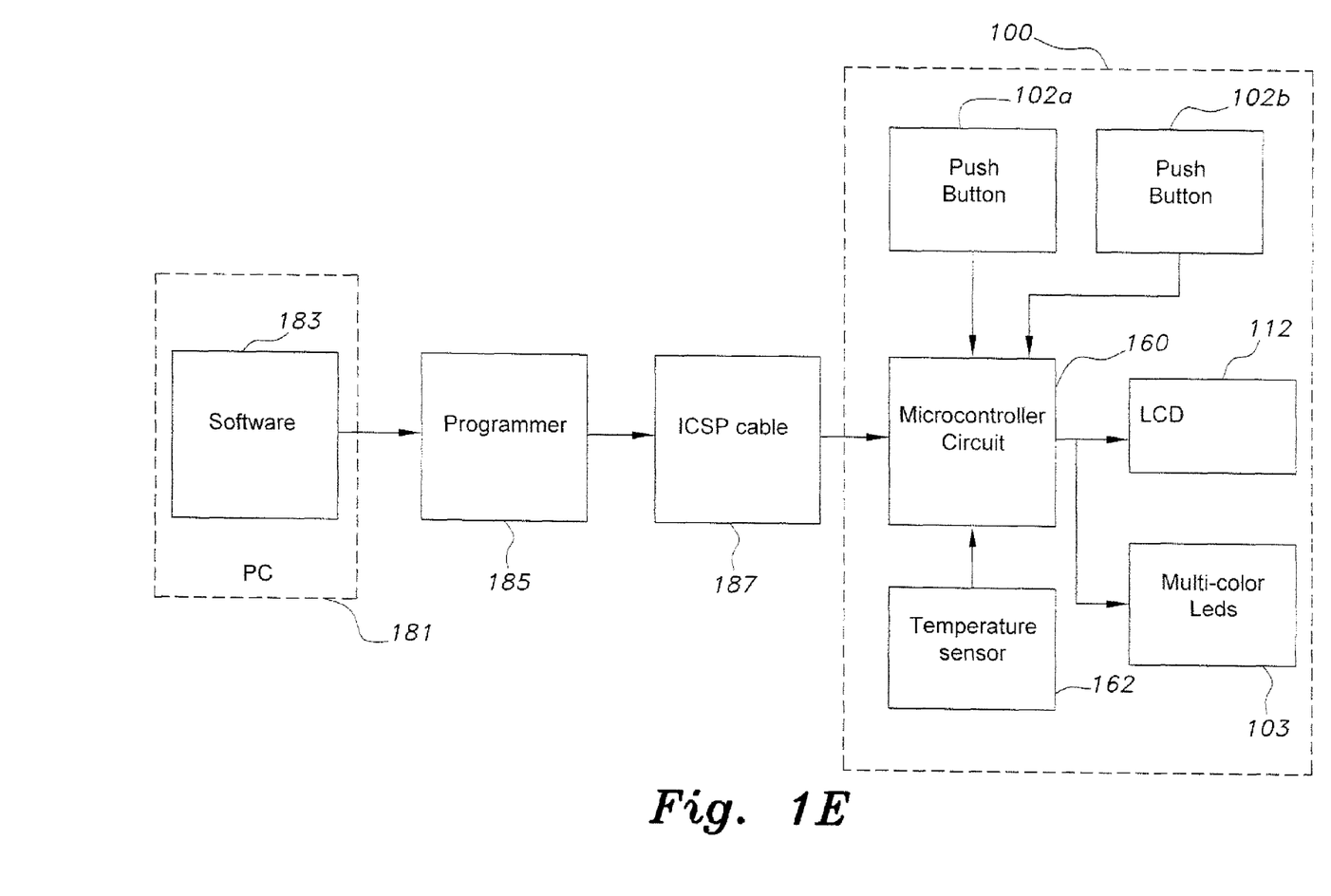
FIG. 1E is a block diagram of an electronic circuit for a medical information band according to the present invention.

As shown in block diagram FIG. 1E, the electronic control unit 100 houses an electronic circuit that includes a microcontroller 160 for automatic control of the internal circuitry. Push buttons 102a and 182b are connected to the microcontroller circuit 160 to provide user control of circuit functions.

The microcontroller 160 is connected to and controls the functioning of the LCD display 112 and the multi-color LED's 103. At least one temperature sensor 162 is connected to the microcontroller, the sensor 162 coordinating alerts and notifications based on a predetermined correct sensed temperature range (there can be a temperature sensor measuring ambient temperature and/or a temperature sensor measuring the wearer's body temperature).

Figure 2:
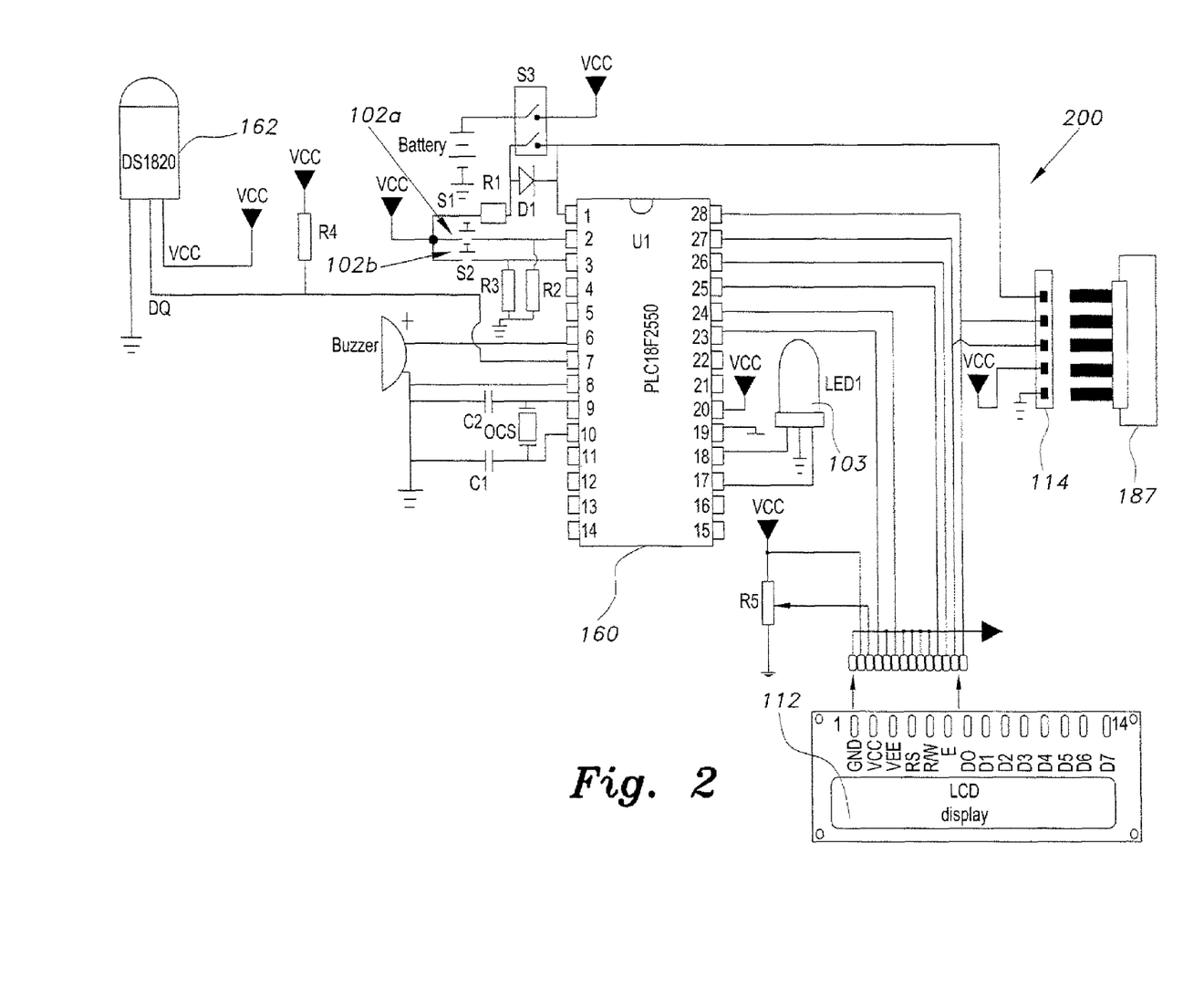
FIG. 2 is a schematic diagram of an electronic circuit for a medical information band according to the present invention.

To facilitate downloading the medical data from a computer 181, an ICSP cable 187 is connected to the microcontroller 160 via the port 114, thereby enabling medical data software programming of the electronic control unit 100 by external programming circuitry 185 that transfers device software 183 developed on a PC 181 to the electronic control unit 100. Alternatively, transfers of program software 183 to the electronic control unit 100 may be accomplished by a USB cable connection of the electronic control unit 100 to the PC 181. A USB connection on the electronic control unit 100 facilitates connection of the electronic control unit 100 to a cellular mobile telephone, for example. In case of using the electronic control unit 100 on a device other than a band, a mini LCD is added to the electronic control unit 100. A schematic of the internal electronic circuit 200 housed in the electronic control unit 100 is shown in FIG. 2.

Moreover, a buzzer or a recorded voice device may be added to the electronic control unit 100 for audible notifications and alarms. The LED's 103 are added to the electronic circuit for a visual alert or alarm.

The electronic control unit 100 can be attached or detached from the band 12 easily to be patched to any other device, such as a mobile phone, or it can be patched on the medicine directly.

The Mini LCD Display 112 Is used to display the functions shown in Table 1.

TABLE 1

Display Functions

| FUNCTION | DISPLAY |
|---|---|
| Expiration Alarm | Displays the expiration date and the time left to use it in addition it will beep if the expiration date is passed |
| Specified Periods Alarm | Displays and alarms the user about the time for taking the drugs. |
| Inappropriate Ambient Temperature Alarm | Displays and alarms the user about the current ambient temperature and recommends the appropriate ambient temperature for the drug. |

If one of the Table 1 functions is passed or not satisfied, a message will be displayed on the LCD 112 to explain what went wrong. For example, in case of expiration alarm, if the expiration date of a medication is passed, a message will be displayed on the LCD 112 indicating, e.g., "Expiration Date is Passed," and at the same time, the LED's 103 will blink. A unique color of multi-color LED's 103 indicates the current function. The Mini LCD 112 can be replaced by a 27-segment or more display, if desired. Moreover, the mini LCD 112 can be removed altogether in order to optimize the cost of the electronic control unit 100.

The push buttons 102a and 102b are used for manual setting of the electronic control unit 100. For example, if we want to increment the expiration date, we push button 102a, but if we want to decrement it, we push button 102b. However, we can move to another function other than expiration date, e.g., the specified periods function, by simply pressing the two buttons 102a and 102b simultaneously. Moreover, we can reset the device in order to delete all the previous information by turning off (removing power from) the band.

The ICSP cable 187 is used to transfer all drug information automatically to the medical information band including the amounts that should be taken for the drug. Next, an automatic transfer of the information to the microcontroller circuit 160 is performed. The newly transferred information is displayed on the LCD 112 without the need of being entered using the push buttons 102a and 102b.

The band 12 is a flexible and stretchable annular ring that carries the electronic control unit 100. The band 12 is preferably made of rubber that stretches to accommodate many wrist sizes.

The microcontroller circuit 160 is the main component in the medical information band. The microcontroller circuit 160 is connected to all sensor and user interface components of the medical information band and analyzes, organizes and processes all the band functions. Referring now to FIG. 2, which shows the circuit 200 in detail, and Table 2, which indicates pin functionality and exemplary component values, the detailed circuitry is disclosed herein.

TABLE 2

Circuit components and values

| Symbol | Name | Value | Function |
|---|---|---|---|
| U1 | microcontroller - PIC61F2550-28 DIP | — | To implement the downloaded hex file on the circuit and it is basically the main item of the circuit |
| LCD | MINI-LCD DISPLAY | — | To display all the massages sent by U1 |
| DS1820 | DS1820 | — | It's the temperature sensor |
| Buzzer | 5 v-Buzzer | — | To generate a continuous or a constant beep sound |
| LED1 | Tow colors LED | — | It's a two color (red and green) light emitting diode which emits a blinking or a constant red or green lights |
| OCS | Crystal 20 MHz Oscillator | 20 MHz | To generates a clock signal and for frequency stabilization |
| D1 | Silicon Diode | — | To prevent the connection between the VCC of the circuit and the VCC of the PC when Uploading the program on U1 |
| C1, C2 | Capacitor | 22 pf | Works with the oscillator to generate a clock signal and for frequency stabilization |
| S1, S2 | Push Button 1, 2 | — | Used for manual calibration |
| S3 | Double Switch | — | It must be turned on when uploading the program from the PC and then Turned OFF after it to prevent the Connection between The Circuit VCC and the PC VCC |
| R1 | Resister | 10 KΩ | Its connected to MCLR pin |
| R2 | Resister | 1 MΩ | To reduce the sensitivity of the push button 1 input by discharge the charges which accumulates on the wire |
| R3 | Resister | 1 MΩ | To reduce the sensitivity of the push button 2 input by discharge the charges that accumulate on the wire |
| R4 | Resister | 10 KΩ | It helps the temperature sensor to work properly |
| R5 | Variable Resister | 5 KΩ | To calibrate the light intensity for the MiniLCD |
| Battery | Battery/Rechargable battery/Solar cell rechargeable battery/Body Heat rechargeable battery | 5 v | It's the power source for the Circuit |

The temperature sensor 162 is used to measure the ambient temperature in order to transform it to electrical signal to be processed in the microcontroller circuit 160.

The digital multi-colored LED's 103 are used for alarming purposes, depending on the conditions shown in Table 3.

TABLE 3

| Condition | Action |
|---|---|
| Case 1: Expiration date is passed | Both LEDs will emit constant red color. |
| Case 2: Specified period is passed | Both LEDs will emit a blinking green color. |
| Case 3: Ambient temperature is not within the drug normal ambient temperature range | Both LEDs will emit a blinking Red color. However; a recorded voice can be used for all of the previous functions for people with vision problems. |

A buzzer (shown in FIG. 2) is connected to the microprocessor 160 and produces a beep sound if the medicine expiration date passes. A recorded voice can also be used for all of the alert functions.

ICSP 187 is connected to ICSP terminal on the programmer 185. The ICSP cable 187 contains a plurality of wires, which connect to corresponding ICSP plug 187 and jack 114, as shown in FIG. 2.

The programmer 185 is a MCUMALL (www.mcumall.com) model PRG-017. The programmer 185 is a USB-PIC programmer, which is used to download the hex file generated by a micro basic code, the hex file being machine loadable instructions and data for microprocessor 160.

The software program used to program this microcontroller is mikroBasic™. The code for this software is written in the Basic language.

To make it easier and smoother in downloading the hex file, a Visual Basic program is used as a user interface, providing data entry fields for the medical information that is uploaded to the device circuitry 100. The user is prompted to enter four main information fields.

Figure 3:
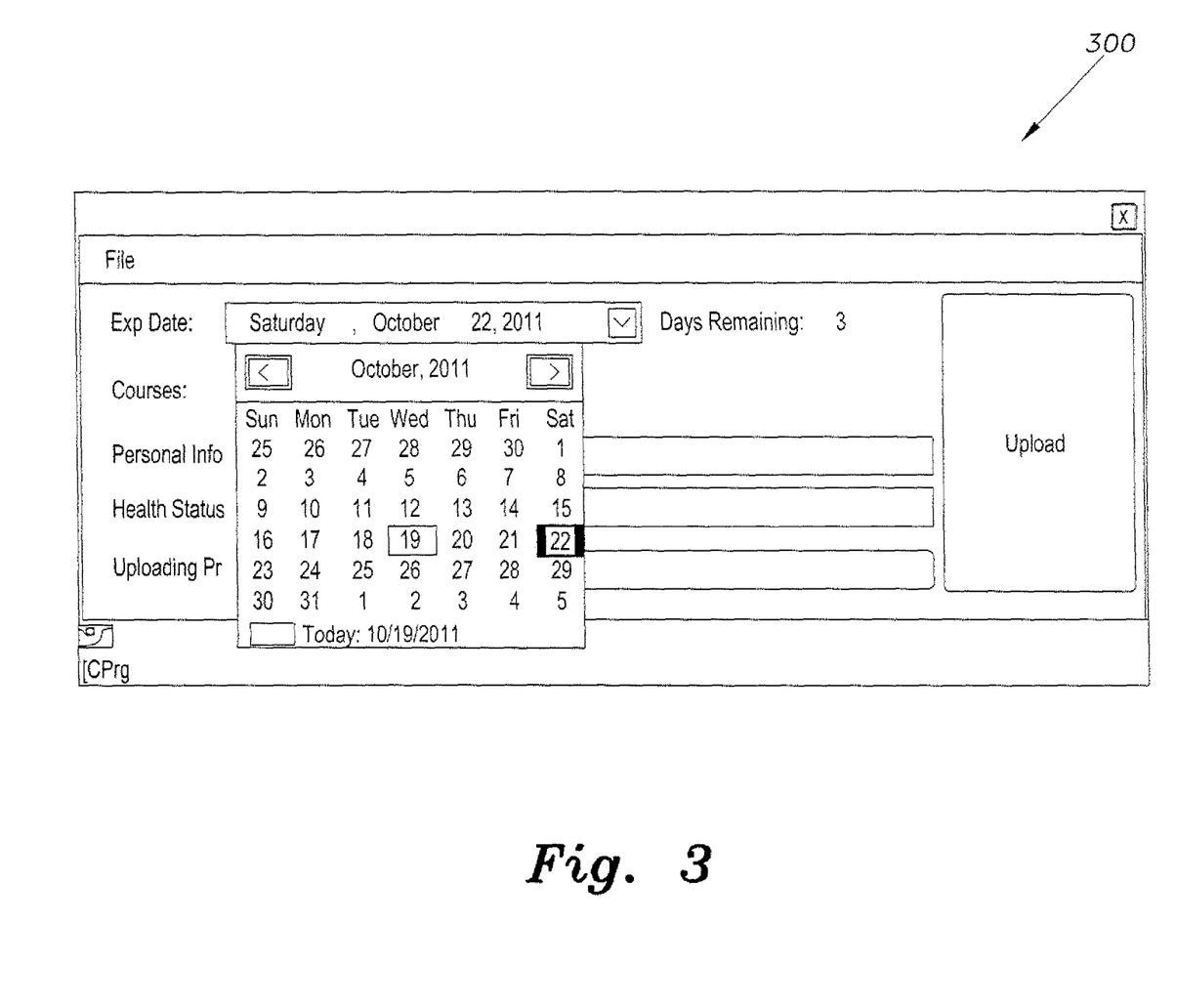
FIG. 3 is a screenshot of a medical information data entry screen and calendar that may be displayed on a medical information band according to the present invention, showing use of the calendar for entry of date information.

The Expiration Date and Notes GUI field 300, as shown in FIG. 3, has a calendar, an expiration date pull down menu, and displays on the calendar a box outline, which refers to the Current date. The Expiration date, selected by the Exp Date pull down menu, is depicted by a shaded box over the calendar's displayed Expiration Date. The Days Remaining field informs the user how many days remain until the drug expiration date. The exemplary expiration date shown is Saturday, Oct. 22, 2011.

Figure 4:
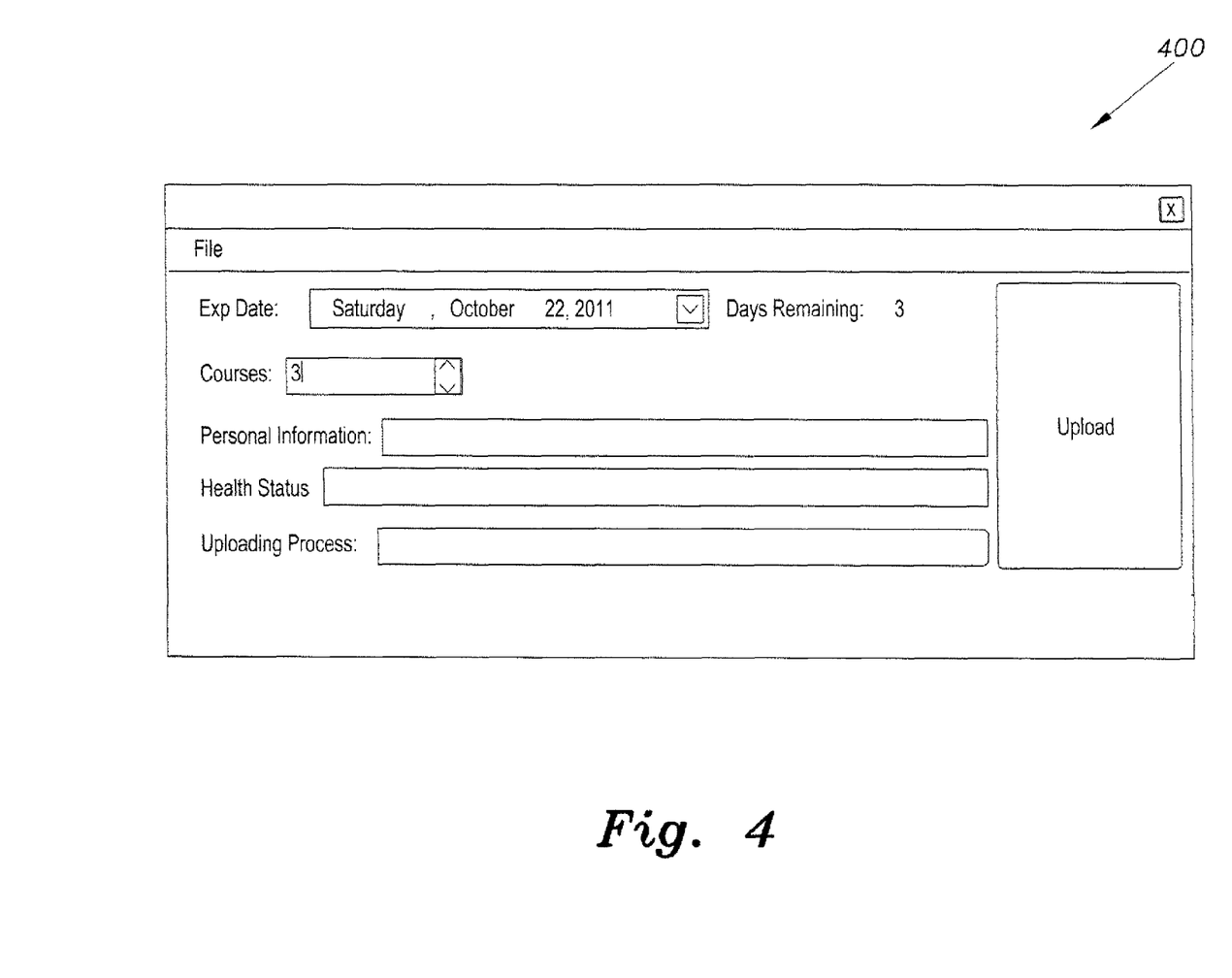
FIG. 4 is a screenshot of the medical information data entry screen that may be displayed on a medical information band according to the present invention.

The Courses GUI field 400, as shown in FIG. 4, has a "Courses:" pull down menu that allows the user to enter/select the number of specified times he should take the drug per day. The exemplary number of Courses shown is "3".

Figure 5:
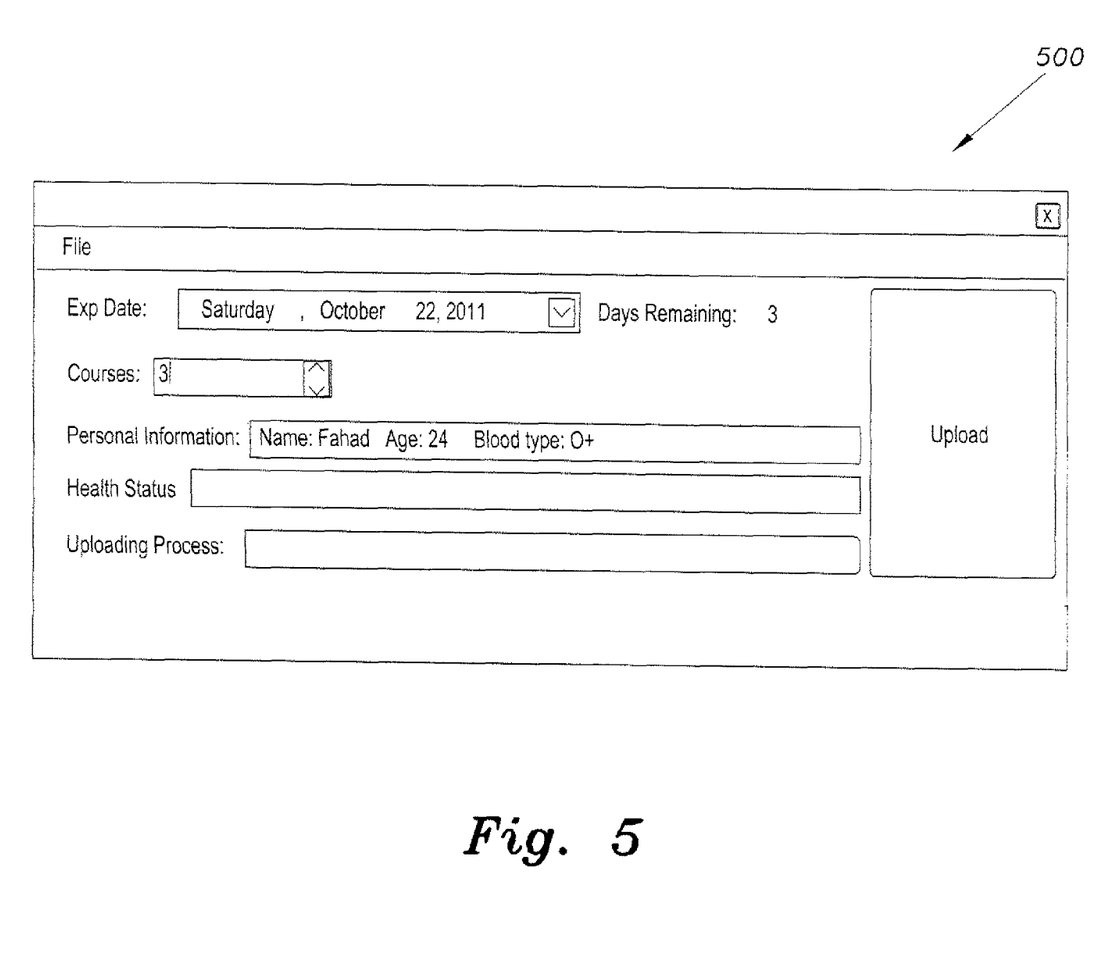
FIG. 5 is a screenshot of the medical information data entry screen that may be displayed on a medical information band according to the present invention, showing exemplary entry of personal information.

The Personal Information GUI field 500, as shown in FIG. 5, has a "Personal Information:" text box field that allows the user to enter his basic main personal information including Name, Age, and Blood Type. The exemplary Personal Information shown is "Name: Fahad Age:24 Blood type: O+".

Figure 6:
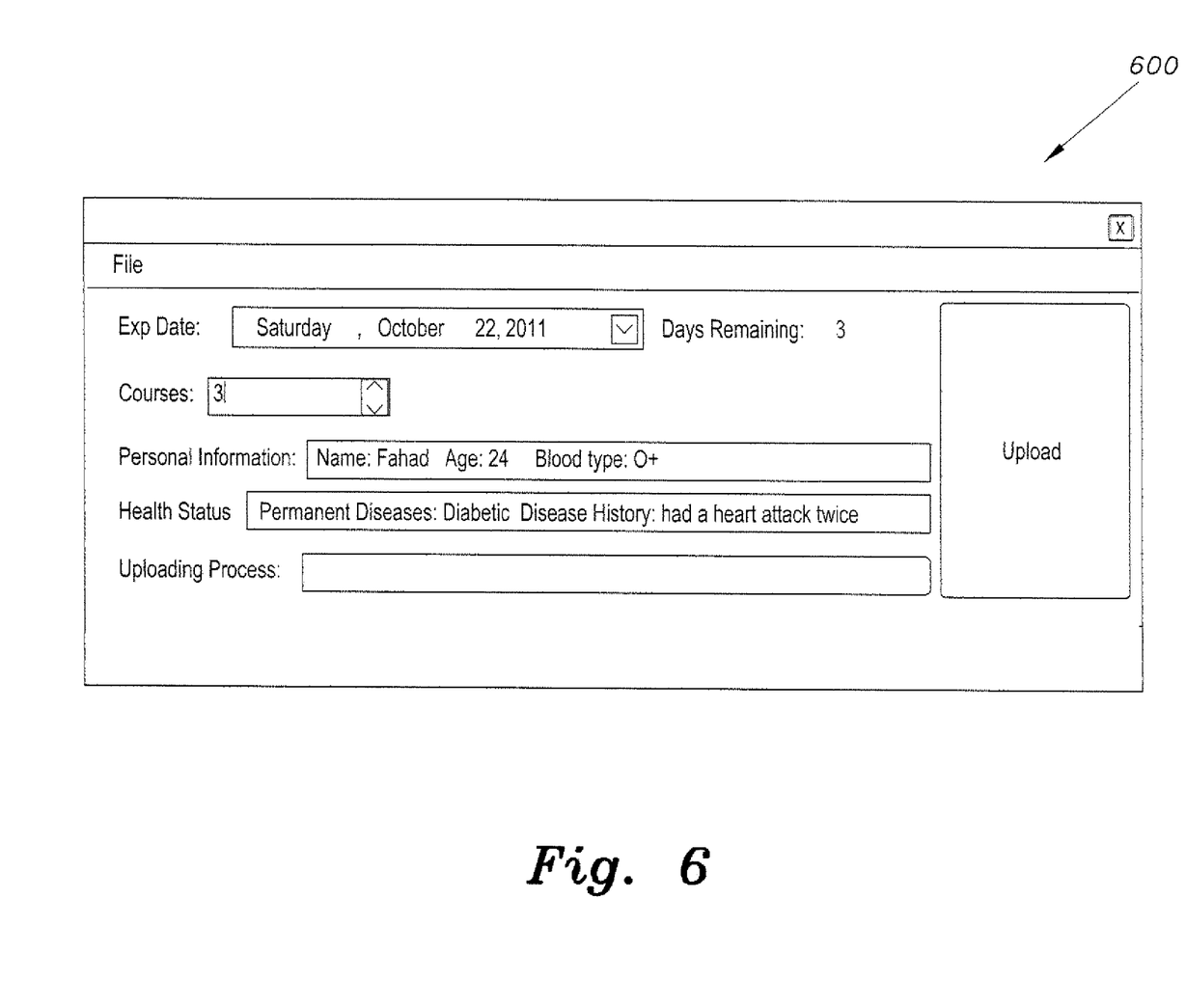
FIG. 6 is a screenshot of the medical information data entry screen that may be displayed on a medical information band according to the present invention, showing exemplary entry of health status information.

The Health Status GUI field 600, as shown in FIG. 6, has a "Health Status" text box field that allows the user to enter any permanent diseases he suffers from. Moreover he may also enter his disease history. The exemplary Health Status shown is "Permanent Diseases: Diabetic Disease History: had a heart attack twice".

When the user is finished entering the aforementioned information he may now click upload then wait for the Uploading Process progress bar to fill up.

In summary, medical information bands have different casings in which it is suitable for different sizes and shapes of drug packaging. The rubber band casing adaptation 10c is designed for round and cylindrical drug containers, or an alternative band casing 10a can be worn on a human wrist as well, whereas the sticker casing 101) can be mounted to any flat surface drugs container. Additionally, the medical information band electronic control unit 100 can be connected to a watch container, i.e., a watchband, for easily adjusting the size, depending on the wearer's wrist size and to get waterproof or airtight property as well.

It is to be understood that the present invention is not limited to the embodiments described above, but encompasses any and all embodiments within the scope of the following claims.

I claim:

1. A computer software product, comprising a non-transitory medium readable by a processor, the non-transitory medium having stored thereon a set of instructions for electronically storing medical and prescription information on a wearable elastic medical information band, the set of instructions including:
   (a) a first sequence of instructions which, when executed by the processor, causes the processor to display ambient temperature sensor data input to the processor;
   (b) a second sequence of instructions which, when executed by the processor, causes the processor to automatically store pharmaceutical data, including correct pharmaceutical dosing instructions and expiration dates input to the processor;
   (c) a third sequence of instructions which, when executed by the processor, causes the processor to display on a display device attached to the band the automatically stored pharmaceutical data;
   (d) a fourth sequence of instructions which, when executed by the processor, causes the processor to alert a user when the pharmaceutical expiration dates occur;
   (e) a fifth sequence of instructions which, when executed by the processor, causes the processor to accept, via an input port, microcode instructions for carrying out all functionality related to the electronically storing of the medical and the prescription information on the elastic band;
   (f) a sixth sequence of instructions which, when executed by the processor, causes the processor to increment and decrement numerical values of the medical and prescription information responsive to input from the user using push buttons attached to the medical information band;
   (g) a seventh sequence of instructions which, when executed by the processor, causes the processor to display to and alert the user of the correct time and dosing instructions for taking the pharmaceutical; and
   (h) an eighth sequence of instructions which, when executed by the processor, causes the processor to display to and alert the user of a sensed current ambient temperature and recommend to the user to move the pharmaceutical to a location having the correct ambient temperature for the pharmaceutical.

2. The computer software product according to claim 1, further comprising a ninth sequence of instructions which, when executed by the processor, causes the processor to sound an audible alarm in conjunction with the expiration dates alert.

3. The computer software product according to claim 2, further comprising a tenth sequence of instructions which, when executed by the processor, causes the processor to play a recorded voice message in conjunction with the expiration dates alert.

4. The computer software product according to claim 3, further comprising an eleventh sequence of instructions which, when executed by the processor, causes the processor to accept the pharmaceutical data from data entry forms provided by another processor.

5. The computer software product according to claim 4, further comprising a twelfth sequence of instructions which, when executed by the processor, causes the processor to accept personal information about the user, the personal information including Name, Age, and Blood Type of the user.

6. The computer software product according to claim 5, further comprising a thirteenth sequence of instructions which, when executed by the processor, causes the processor to accept health status information about the user, the health status information including:
   any chronic conditions the user suffers from; and
   any historic medical conditions the user has suffered from.

7. The computer software product according to claim 6, further comprising a fourteenth sequence of instructions which, when executed by the processor, causes the processor to display the health status information, including any chronic conditions the user suffers from and any historic medical conditions the user has suffered from, the pharmaceutical dosing instructions, and the personal information about the user in response to a predetermined button push sequence of said push buttons.

8. The computer software product according to claim 7, further comprising a fifteenth sequence of instructions which, when executed by the processor, causes the processor to actuate light emitters on said medical information band to a constant predetermined first color when the expiration date has passed, to a blinking predetermined second color when a user-specified period of time has elapsed, the user-specified period of time being the interval between prescribed dosage times of the pharmaceutical, and to a blinking predetermined first color when the ambient temperature is not within the pharmaceutical's normal ambient temperature range.

9. A medical information band, comprising:
an elastic band adapted for being worn by a user;
an electronic control unit removably attached to the elastic band;
an electronic digital circuit for storing medical and prescription information entered by a user, the circuit being housed in the electronic control unit;
an electronic display mounted in the electronic control unit, the display being connected to the electronic digital circuit;
an ambient temperature sensor disposed in the electronic control unit, the temperature sensor being connected to the electronic digital circuit;
means for automatically storing pharmaceutical data, including correct pharmaceutical dosing instructions and expiration dates input, in the electronic digital circuit;
means for displaying the automatically stored pharmaceutical data on the electronic display;
means for alerting a user when the pharmaceutical expiration dates occur;
an input port connected to the electronic digital circuit, the input port being adapted for transmission of microcode instructions for carrying out all functionality related to electronic storing of the medical and prescription information to the electronic digital circuit;
push buttons mounted on the electronic control unit, the push buttons being in operable communication with the electronic digital circuit;
means for incrementing and decrementing numerical values of the medical and prescription information responsive to input from the user using the push buttons;
means for displaying to and alerting the user of the correct time and dosing instructions for taking the pharmaceutical; and
means for displaying to and alerting the user of a sensed current ambient temperature and means for recommending to the user to move the pharmaceutical to a location having the correct ambient temperature for the pharmaceutical.

10. The medical information band according to claim 9, further comprising means for sounding an audible alarm in conjunction with the expiration dates alert.

11. The medical information band according to claim 10, further comprising means for playing a recorded voice message in conjunction with the expiration dates alert.

12. The medical information band according to claim 11, further comprising means for accepting the pharmaceutical data from data entry forms provided by another processor.

13. The medical information band according to claim 12, further comprising means for accepting personal information about the user, the personal information including Name, Age, and Blood Type of the user.

14. The medical information band according to claim 13, further comprising means for accepting health status information about the user, the health status information including:
any chronic conditions the user suffers from; and
any historic medical conditions the user has suffered from.

15. The medical information band according to claim 14, further comprising means for displaying the health status information, the pharmaceutical dosing instructions, and the personal information about the user on the electronic display based on a predetermined operational sequence of said push buttons.

16. The medical information band according to claim 15, further comprising:
a plurality of light emitting diodes disposed on the electronic control unit, the diodes being in operable communication with said electronic digital circuit;
means for actuating the light emitting diodes to a constant predetermined first color when the expiration date has passed, to a blinking predetermined second color when a user-specified period of time has elapsed, the user-specified period of time being the interval between prescribed dosage times of the pharmaceutical, and to a blinking predetermined first color when the ambient temperature is not within the pharmaceutical's normal ambient temperature range.

17. The medical information band according to claim 16, further comprising means for attaching said electronic control unit to a pharmaceutical package.

* * * * *